United States Patent

Kassem

(10) Patent No.: US 9,204,812 B2
(45) Date of Patent: Dec. 8, 2015

(54) WIRELESS PRESSURE SENSING SHUNTS

(75) Inventor: Salim Kassem, North Attleboro, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1106 days.

(21) Appl. No.: 11/931,151

(22) Filed: Oct. 31, 2007

(65) Prior Publication Data

US 2009/0112103 A1    Apr. 30, 2009

(51) Int. Cl.
*A61B 5/021* (2006.01)
*A61B 5/03* (2006.01)
*A61B 5/00* (2006.01)
*A61M 27/00* (2006.01)

(52) U.S. Cl.
CPC .............. *A61B 5/031* (2013.01); *A61B 5/0031* (2013.01); *A61M 27/006* (2013.01)

(58) Field of Classification Search
USPC ............... 600/488, 486, 485, 561, 302; 604/9
See application file for complete search history.

(56) References Cited

U.S. PATENT DOCUMENTS

| | | |
|---|---|---|
| 2,396,351 A | 3/1946 | Thompson |
| 3,886,948 A | 6/1975 | Hakim et al. |
| 3,960,142 A | 6/1976 | Elliott et al. |
| 3,976,278 A | 8/1976 | Dye et al. |
| 4,077,882 A | 3/1978 | Gangemi |
| 4,114,603 A | 9/1978 | Wilkinson |
| 4,127,110 A | 11/1978 | Bullara |
| 4,135,509 A | 1/1979 | Shannon |
| 4,237,900 A | 12/1980 | Schulman et al. |

(Continued)

FOREIGN PATENT DOCUMENTS

| | | |
|---|---|---|
| AU | 729467 | 2/2001 |
| CN | 2555770 Y | 6/2003 |

(Continued)

OTHER PUBLICATIONS

U.S. Office Action for U.S. Appl. No. 11/931,041 (Publication No. US-2009-0107233-A1) dated Dec. 30, 2009, 19 pages.

(Continued)

*Primary Examiner* — Patricia Mallari
*Assistant Examiner* — Michael Catina
(74) *Attorney, Agent, or Firm* — Mintz Levin Cohn Ferris Glovsky and Popeo, P.C.

(57) ABSTRACT

Devices and methods useful for sensing or measuring a pressure and remotely indicating or communicating that pressure are provided. The devices and methods have particular utility in sensing pressures in implantable medical devices and more particularly in hydrocephalus shunts. In one exemplary embodiment, an implantable valve can include a housing having a reservoir adapted to receive fluid flow therethrough between an inlet port and an outlet port. The implantable valve can also include a needle-penetrable septum to allow fluid delivery to the reservoir and/or a needle guard disposed within the housing and adapted to protect the radio frequency tag from a needle penetrating into the housing. A radio frequency (RF) tag can be disposed within the reservoir and can be adapted to change one or more of its electromagnetic characteristics in response pressure applied thereto by fluid in or flowing through the reservoir. The RF tag can produce a response to a wireless signal characterized by the one or more electromagnetic characteristics that correlates to a pressure of fluid in or flowing through the reservoir.

6 Claims, 8 Drawing Sheets

(56) References Cited

U.S. PATENT DOCUMENTS

| | | | |
|---|---|---|---|
| 4,332,255 A | 6/1982 | Hakim et al. | |
| 4,385,636 A * | 5/1983 | Cosman | 600/561 |
| 4,387,715 A | 6/1983 | Hakim et al. | |
| 4,421,124 A | 12/1983 | Marshall | |
| 4,494,950 A | 1/1985 | Fischell | |
| 4,540,400 A | 9/1985 | Hooven | |
| 4,551,128 A | 11/1985 | Hakim et al. | |
| 4,556,086 A | 12/1985 | Raines | |
| 4,576,181 A | 3/1986 | Wallace et al. | |
| 4,593,703 A * | 6/1986 | Cosman | 600/561 |
| 4,595,390 A | 6/1986 | Hakim et al. | |
| 4,611,578 A | 9/1986 | Heimes et al. | |
| 4,615,691 A | 10/1986 | Hakim et al. | |
| 4,625,730 A | 12/1986 | Fountain et al. | |
| 4,660,568 A | 4/1987 | Cosman | |
| 4,676,772 A | 6/1987 | Hooven | |
| 4,711,249 A | 12/1987 | Brooks | |
| 4,718,425 A | 1/1988 | Tanaka et al. | |
| 4,723,556 A | 2/1988 | Sussman | |
| 4,727,887 A | 3/1988 | Haber | |
| 4,772,257 A | 9/1988 | Hakim et al. | |
| 4,785,822 A | 11/1988 | Wallace | |
| 4,787,886 A | 11/1988 | Cosman | |
| 4,820,265 A | 4/1989 | DeSatnick et al. | |
| 4,841,977 A | 6/1989 | Griffith et al. | |
| 4,850,358 A | 7/1989 | Millar | |
| 4,885,002 A | 12/1989 | Watanabe et al. | |
| 4,893,630 A | 1/1990 | Bray, Jr. | |
| 5,004,472 A | 4/1991 | Wallace | |
| 5,009,662 A | 4/1991 | Wallace et al. | |
| 5,021,046 A | 6/1991 | Wallace | |
| 5,163,904 A | 11/1992 | Lampropoulos et al. | |
| 5,201,753 A | 4/1993 | Lampropoulos et al. | |
| 5,252,962 A | 10/1993 | Urbas et al. | |
| 5,265,606 A | 11/1993 | Kujawski | |
| 5,280,789 A | 1/1994 | Potts | |
| 5,321,989 A | 6/1994 | Zimmer et al. | |
| 5,337,612 A | 8/1994 | Evans | |
| 5,385,514 A | 1/1995 | Dawe | |
| 5,396,899 A | 3/1995 | Strittmatter | |
| 5,417,235 A | 5/1995 | Wise et al. | |
| 5,425,713 A | 6/1995 | Taylor et al. | |
| 5,431,057 A | 7/1995 | Zimmer et al. | |
| 5,431,629 A | 7/1995 | Lampropoulos et al. | |
| 5,437,627 A * | 8/1995 | Lecuyer | 604/9 |
| 5,449,345 A | 9/1995 | Taylor et al. | |
| 5,490,514 A | 2/1996 | Rosenberg | |
| 5,591,171 A | 1/1997 | Brown | |
| 5,622,869 A | 4/1997 | Lewis et al. | |
| 5,630,836 A | 5/1997 | Prem et al. | |
| 5,643,194 A | 7/1997 | Negre | |
| 5,651,767 A * | 7/1997 | Schulman et al. | 604/8 |
| 5,704,352 A * | 1/1998 | Tremblay et al. | 600/300 |
| 5,711,302 A | 1/1998 | Lampropoulos et al. | |
| 5,716,342 A | 2/1998 | Dumbraveanu et al. | |
| 5,721,382 A | 2/1998 | Kriesel et al. | |
| 5,797,403 A | 8/1998 | DiLorenzo | |
| 5,803,917 A | 9/1998 | Butterfield et al. | |
| 5,836,886 A | 11/1998 | Itoigawa et al. | |
| 5,873,840 A | 2/1999 | Neff | |
| 5,928,182 A * | 7/1999 | Kraus et al. | 604/9 |
| 5,935,083 A | 8/1999 | Williams | |
| 5,970,801 A | 10/1999 | Ciobanu et al. | |
| 5,993,395 A | 11/1999 | Shulze | |
| 5,993,398 A | 11/1999 | Alperin | |
| 6,010,482 A | 1/2000 | Kriesel et al. | |
| 6,025,725 A | 2/2000 | Gershenfeld et al. | |
| 6,071,267 A | 6/2000 | Zamierowski | |
| 6,083,174 A | 7/2000 | Brehmeier-Flick et al. | |
| 6,111,520 A | 8/2000 | Allen et al. | |
| 6,113,553 A | 9/2000 | Chubbuck | |
| 6,120,457 A | 9/2000 | Coombes et al. | |
| 6,158,965 A | 12/2000 | Butterfield et al. | |
| 6,171,252 B1 | 1/2001 | Roberts | |
| 6,208,254 B1 | 3/2001 | McQueen et al. | |
| 6,248,080 B1 | 6/2001 | Miesel et al. | |
| 6,264,612 B1 | 7/2001 | McConnell et al. | |
| 6,278,379 B1 | 8/2001 | Allen et al. | |
| 6,316,522 B1 | 11/2001 | Loomis et al. | |
| 6,371,976 B1 | 4/2002 | Vrzalik et al. | |
| 6,416,291 B1 | 7/2002 | Butterfield et al. | |
| 6,439,538 B1 | 8/2002 | Ito | |
| 6,447,449 B1 * | 9/2002 | Fleischman et al. | 600/405 |
| 6,470,213 B1 | 10/2002 | Alley | |
| 6,481,292 B1 | 11/2002 | Reich | |
| 6,503,208 B1 | 1/2003 | Skovlund et al. | |
| 6,533,733 B1 * | 3/2003 | Ericson et al. | 600/561 |
| 6,537,232 B1 | 3/2003 | Kucharczyk et al. | |
| 6,589,189 B2 | 7/2003 | Meyerson et al. | |
| 6,626,902 B1 | 9/2003 | Kucharczyk et al. | |
| 6,636,769 B2 | 10/2003 | Govari et al. | |
| 6,682,490 B2 | 1/2004 | Roy et al. | |
| 6,724,310 B1 | 4/2004 | Gershenfeld et al. | |
| 6,731,976 B2 | 5/2004 | Penn et al. | |
| 6,770,030 B1 | 8/2004 | Schaupp et al. | |
| 6,796,942 B1 * | 9/2004 | Kreiner et al. | 600/398 |
| 6,855,115 B2 * | 2/2005 | Fonseca et al. | 600/488 |
| 6,891,474 B1 | 5/2005 | Fletcher | |
| 6,974,422 B1 * | 12/2005 | Millar | 600/561 |
| 7,147,604 B1 * | 12/2006 | Allen et al. | 600/549 |
| 7,435,229 B2 | 10/2008 | Wolf | |
| 7,842,004 B2 | 11/2010 | Kassem | |
| 2002/0035331 A1 | 3/2002 | Brockway et al. | |
| 2002/0038072 A1 * | 3/2002 | Muller et al. | 600/25 |
| 2002/0052563 A1 | 5/2002 | Penn et al. | |
| 2002/0077553 A1 | 6/2002 | Govari et al. | |
| 2002/0087059 A1 | 7/2002 | O'keefe | |
| 2002/0099428 A1 | 7/2002 | Kaufman | |
| 2002/0151770 A1 | 10/2002 | Noll et al. | |
| 2003/0023134 A1 | 1/2003 | Tracey | |
| 2003/0032915 A1 | 2/2003 | Saul | |
| 2003/0135110 A1 | 7/2003 | Leussler | |
| 2003/0216666 A1 | 11/2003 | Ericson et al. | |
| 2004/0073137 A1 | 4/2004 | Lloyd et al. | |
| 2004/0134991 A1 | 7/2004 | Fletcher et al. | |
| 2004/0147871 A1 | 7/2004 | Burnett | |
| 2004/0193021 A1 | 9/2004 | Zdeblick et al. | |
| 2004/0260229 A1 * | 12/2004 | Meir | 604/9 |
| 2005/0027330 A1 | 2/2005 | Govari | |
| 2005/0043669 A1 | 2/2005 | Rosenberg | |
| 2005/0043670 A1 | 2/2005 | Rosenberg | |
| 2005/0165317 A1 | 7/2005 | Turner et al. | |
| 2005/0187487 A1 | 8/2005 | Azizkhan et al. | |
| 2005/0187488 A1 | 8/2005 | Wolf | |
| 2005/0187509 A1 | 8/2005 | Wolf | |
| 2005/0197585 A1 | 9/2005 | Brockway et al. | |
| 2005/0204811 A1 | 9/2005 | Neff | |
| 2005/0277839 A1 | 12/2005 | Alderman et al. | |
| 2006/0009699 A1 | 1/2006 | Roteliuk et al. | |
| 2006/0020239 A1 * | 1/2006 | Geiger et al. | 604/9 |
| 2006/0036208 A1 | 2/2006 | Burnett | |
| 2006/0149161 A1 | 7/2006 | Wilson et al. | |
| 2006/0189888 A1 | 8/2006 | Hassler et al. | |
| 2006/0195043 A1 | 8/2006 | Rutherford et al. | |
| 2006/0211944 A1 | 9/2006 | Mauge et al. | |
| 2006/0211945 A1 | 9/2006 | Mauge et al. | |
| 2006/0211946 A1 * | 9/2006 | Mauge et al. | 600/488 |
| 2006/0235310 A1 | 10/2006 | O'Brien et al. | |
| 2006/0283007 A1 | 12/2006 | Cros et al. | |
| 2007/0049845 A1 | 3/2007 | Fleischman et al. | |
| 2007/0118038 A1 * | 5/2007 | Bodecker et al. | 600/486 |
| 2007/0167867 A1 * | 7/2007 | Wolf | 600/561 |
| 2007/0208293 A1 * | 9/2007 | Mansour et al. | 604/9 |
| 2007/0210923 A1 | 9/2007 | Butler et al. | |
| 2007/0282210 A1 | 12/2007 | Stern | |
| 2008/0058652 A1 * | 3/2008 | Payne | 600/488 |
| 2008/0139959 A1 | 6/2008 | Miethke et al. | |
| 2008/0208083 A1 | 8/2008 | Lin et al. | |
| 2009/0107233 A1 | 4/2009 | Kassem | |

(56) References Cited

U.S. PATENT DOCUMENTS

| 2009/0112147 A1 | 4/2009 | Kassem |
| 2009/0112308 A1 | 4/2009 | Kassem |
| 2010/0168673 A1 | 7/2010 | Stergiopulos et al. |

FOREIGN PATENT DOCUMENTS

| DE | 4042335 | | 8/1991 |
| DE | 4042336 | | 8/1991 |
| EP | 0115548 | | 8/1984 |
| EP | 0619101 | | 10/1994 |
| EP | 1312302 | | 5/2003 |
| EP | 1389477 | | 2/2004 |
| EP | 1491137 | | 12/2004 |
| EP | 1738792 | A1 | 1/2007 |
| JP | 2003821 | A | 1/1990 |
| WO | WO-9105575 | | 5/1991 |
| WO | WO-9953990 | A1 | 10/1999 |
| WO | 0121066 | A1 | 3/2001 |
| WO | 2005046467 | A1 | 5/2005 |
| WO | 2006048664 | | 5/2006 |
| WO | WO-2006117123 | | 11/2006 |
| WO | 2007041843 | A1 | 4/2007 |
| WO | 2007081741 | | 7/2007 |

OTHER PUBLICATIONS

Ekstedt, J., "CSFS Hydrodynamic Studies in Man, 1. Method of Constant Pressure CSF Infusion," J. Neurology, Neurosurgery & Psych.40:105-19 (1977).

European Search Report, Appl. No. 052580800.0, dated May 15, 2006.

Shapiro, K. et al. "Characterization of Clinical CSF Dynamics and Neural Zxis Compliance Using the Pressure-Volume Index: 1. The Normal Pressure-Volume Index," Annals of Neurology, 7(6):508-14 (1980).

"User's Manual HD2114.0-HD2134.0, HD2164.0-HD2114B.0, HD2114, 2-HD2134.2, HD2164.2-HD2114B.2; Rev. 1.0," Delta OHM, Via g. Marconi, 5-35020 Caselle Di Selvazzano (PD)—Italy, pp. 2-6 (2004).

Dobkin et al., "A Radio-Oriented Introduction to RFID-Protocols, Tags and Applications," High Frequency Electronics, 32-46 (2005).

European Search Report, EP Application No. 08253554, Mailed Feb. 19, 2009.

U.S. Office Action for U.S. Appl. No. 11/931,187 dated May 11, 2010, 8 pages.

U.S. Office Action for U.S. Appl. No. 11/931,187 dated May 9, 2011, 7 pages.

Ko et al: "Cerebrospinal Fluid Control System," Proceeding of the IEEE, IEEE. New York, US, vol. 76, No. 9, Sep. 1, 1988, pp. 1226-1235, XP000094517 ISSN: 0018-9219.

European Search Report, EP Application No. 08253545.1-1526, Mailed Mar. 5, 2009.

U.S. Office Action for U.S. Appl. No. 11/931,187 dated Oct. 6, 2010, 8 pages.

J.S. Kroin, et al., "Long-term testing of an intracranial pressure monitoring device", J. Neurosurg, V. 93, pp. 852-858, 2000.

"Sensor Transponder for Pressure and Temperature", data sheet of Institut Mikroelektronische Schaultungen und Systeme, pp. 1-2, Feb. 2000.

"Telemetric Integrated Pressure Sensors", product data sheet of Institut Mikroelektronische Schaultungen und Systeme, p. 1, Sep. 2002.

"Surface Micromachined Pressure Sensor Technologies", product data sheet of Institut Mikroelektronische Schaultungen und Systeme, pp. 1-2, Sep. 2002.

U.S. Office Action for U.S. Appl. No. 12/913,054 dated Nov. 26, 2012 (11 Pages).

U.S. Office Action for U.S. Appl. No. 11/931,187 dated Apr. 24, 2012 (10 Pages).

U.S. Office Action for U.S. Appl. No. 11/931,127 dated May 10, 2012 (26 Pages).

U.S. Office Action for U.S. Appl. No. 11/931,187, dated Oct. 31, 2011.

* cited by examiner

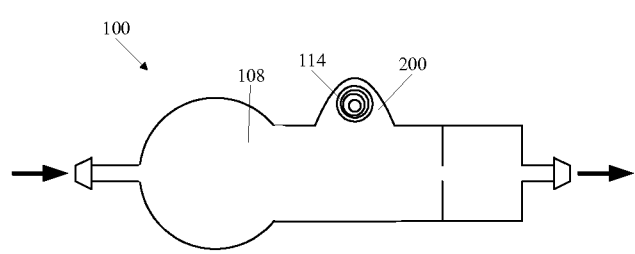
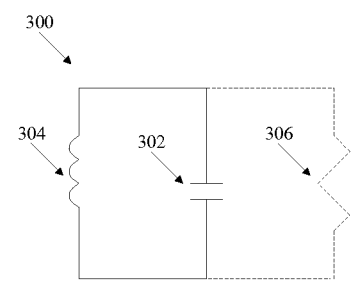
FIG. 2
FIG. 3
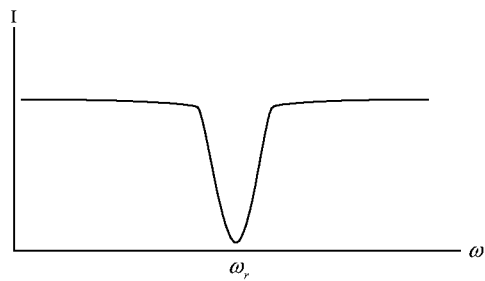
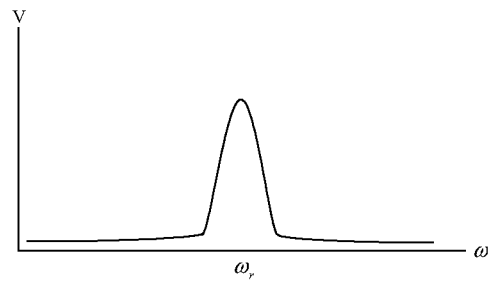
FIG. 4
FIG. 5

WIRELESS PRESSURE SENSING SHUNTS

FIELD OF THE INVENTION

The present invention generally relates to pressure sensors, and more particularly to pressure-sensing shunts.

BACKGROUND

Sensing pressure is useful for a variety of medical purposes. For example, treatment of hydrocephalus can involve monitoring the pressure of cerebrospinal fluid (CSF). Hydrocephalus is a neurological condition that is caused by the abnormal accumulation of CSF within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intra-ventricular or intra-cranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The pressure within the shunt valve, which can resemble the intra-ventricular pressure, may need to be measured and the results non-invasively communicated to a remote device.

Current pressure sensors are often large, particularly relative to the size of a shunt valve, involve complex circuitry for measurement or communication, and consume an inordinate amount of power. Accordingly, there remains a need for a pressure sensor effective to measure pressure within a body or within an implanted medical device, such as a implanted hydrocephalus shunt valve.

SUMMARY

In one embodiment, an implantable valve is provided. The implantable valve can include a housing having a reservoir adapted to receive fluid flow therethrough between an inlet port and an outlet port. The implantable valve can also include a substrate disposed within the reservoir. A radio frequency (RF) tag can be disposed on the substrate within the reservoir and can include circuitry adapted to change one or more electromagnetic characteristics in response to pressure applied thereto by fluid in the reservoir and can be adapted to produce a response to a wireless signal characterized by the one or more electromagnetic characteristics that correlates to a pressure of fluid in the reservoir, as well as a memory for storing data, which can reside on the same substrate as the circuitry adapted to change one or more electromagnetic characteristics in response to pressure applied thereto. For example, the one or more electromagnetic characteristics can be resonant frequency, harmonic spectra, or Q factor. In some embodiments, the pressure of fluid in the reservoir can detectably change any of the shape and the capacitance of the radio frequency tag so as to change the one or more electromagnetic characteristics thereof. Moreover, the circuitry in the radio frequency tag can include an inductor and a capacitor connected to form an electrical circuit having a resonant frequency, the capacitor comprising a pair of conductors separated by a dielectric. The pressure of fluid in the reservoir can detectably change a distance between the pair of conductors. The distance between the pair of conductors can correlate to any of the resonant frequency, harmonic spectra, and Q factor of the electric circuit.

A wide array of variations are possible. The radio frequency tag can have an antenna that is adapted to communicate with an external reading device and to provide a response that correlates to the pressure of fluid flowing through the reservoir. The radio frequency tag can also include digital logic circuitry which can reside on the same substrate as the memory. In some embodiments, the stored data can include any of sensor identification data, sensed pressure data, and patient data.

In other embodiments, the implantable valve can include a valve assembly disposed within the housing and adapted to control a rate of fluid flowing through the housing. The radio frequency tag can be adapted to measure a pressure of fluid flowing through the valve assembly.

In another embodiment, an implantable valve is provided which has a housing defining a reservoir for receiving fluid flow therethrough. A valve assembly can be disposed in the housing and adapted to control a rate of fluid flow through the reservoir. In addition, a substrate can be disposed in said reservoir. A radio frequency tag can be disposed on the substrate in the reservoir and can include circuitry adapted to measure a pressure of fluid in the reservoir and to indicate the measured pressure via at least one electromagnetic characteristic of the radio frequency tag, and can further include a memory for storing data, the memory residing on the same substrate as the circuitry adapted to measure the pressure of fluid. For example, the electromagnetic characteristic can be resonant frequency, harmonic spectra, and Q factor. In some embodiments, the radio frequency tag can be adapted to store data and to communicate stored data to an external reading device. In other embodiments, the radio frequency tag can include an antenna adapted to communicate to an external reading device. The radio frequency tag can be adapted to communicate a radio frequency having the at least one electromagnetic characteristic to the external reading device upon receipt of a wireless signal from the external reading device.

In some embodiments, the pressure of fluid in the reservoir can detectably change the shape of the radio frequency tag so as to change the at least one electromagnetic characteristic of the radio frequency tag. For example, the circuitry in the radio frequency tag can include an inductor and a capacitor connected to form an electrical circuit having a resonant frequency, the capacitor comprising a pair of conductors separated by a dielectric. The pressure of fluid in the reservoir can detectably change a distance between the pair of conductors. The distance between the pair of conductors can correlate to any of the resonant frequency, harmonic spectra, and Q factor of the electric circuit.

In other aspects, an exemplary method for measuring ventricular pressure is provided. The method can include positioning a distal end of a ventricular catheter within a patient's ventricle. The method can further include coupling a proximal end of the ventricular catheter to a valve inlet formed on an implantable valve, and coupling a valve outlet formed on the valve to a drainage catheter such that fluid flows from the ventricle through a reservoir in the valve to the drainage catheter. A rate of fluid flowing through the valve can be controlled by a valve assembly disposed within the implantable valve. The method can also include obtaining a pressure measurement of a pressure of fluid in the valve by detecting a electromagnetic characteristic of a response of a radio frequency tag associated with the valve. The method can also include storing data in a memory in the radio frequency tag. In some embodiments, obtaining the pressure measurement comprises wirelessly receiving a response from the radio frequency tag to a signal and detecting at least one electromagnetic characteristic. For example, the electromagnetic characteristic can be resonant frequency, harmonic spectra, or Q factor. Obtaining the pressure measurement can include detecting a change in one or more electromagnetic characteristics. In some embodiments, obtaining the pressure measurement can include wirelessly transmitting a signal to the radio frequency tag and measuring power received from the radio frequency tag. The signal can be distributed over a plurality of frequencies. In other embodiments, obtaining the pressure measurement includes wirelessly transmitting a signal to the radio frequency tag and measuring the resulting harmonic spectrum. In many embodiments, the radio frequency tag can include circuitry having a resonance frequency for sending pressure and, on the same substrate, a memory for storing data.

BRIEF DESCRIPTION OF THE DRAWINGS

The invention will be more fully understood from the following detailed description taken in conjunction with the accompanying drawings, in which:

FIG. 2 is a schematic view of another embodiment of an implantable valve;

FIG. 3 is a schematic diagram of a resonator circuit;

FIG. 4 is a graph of an output current signal as a function of frequency for the circuit of FIG. 3;

FIG. 5 is a graph of an output voltage signal as a function of frequency for the circuit of FIG. 3;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

Generally, methods and devices for sensing pressure, and in particular for sensing pressure within an implantable medical device such as a hydrocephalus shunt, are provided. In certain exemplary embodiments, the methods and devices can be particularly useful in that they can allow for non-invasive, instantaneous, and/or continuous monitoring of intra-ventricular pressure, thereby reducing risk of infections from invasive monitoring and improving the ability and speed of diagnosing problems within a shunt, such as valve blockage. The methods and devices disclosed herein can provide a compact and low-power sensor that can easily be incorporated into a wide range of medical devices. A person skilled in the art will appreciate that, while the devices and methods are described in connection with an implantable shunt valve, this is by way of illustration only. The device and methods can be used for a variety of medical procedures to measure the pressure in a variety of areas of the body and/or in a variety of devices. Furthermore, a person having ordinary skill in the art will appreciate that the implantable valve can have a variety of other configurations.

Figure 1:
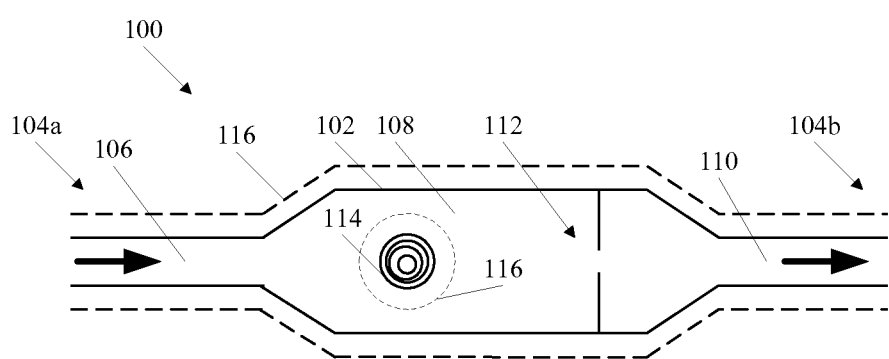
FIG. 1 is a schematic view of an exemplary embodiment of an implantable valve.

While the implantable valve 100 can have virtually any configuration, and a variety of implantable valves known in the art can be used, as shown in FIG. 1 the implantable valve 100 has a valve housing 102 with proximal and distal ends 104a, 104b. The housing 102 can have virtually any configuration, shape, and size, preferably one making the housing 102 suitable for subcutaneous implantation. Fluid (e.g., CSF) can flow through the housing 102 from an inlet (fluid entry) port 106 at the proximal end 104a, through a reservoir 108 and out an outlet (fluid exit) port 110 at the distal end 104b. The location and size of the ports 106, 110 can vary, but in many embodiments they can be adapted to allow fluid to flow therethrough and into and out of the housing 102. The proximal and distal ends 104a, 104b of the valve 100 can each be open and adapted to couple to another medical device, such as a catheter. The valve housing 102 can contain a valve assembly 112 for controlling the flow of fluid from the inlet port 106 to the outlet port 110, and a pressure sensor assembly for measuring a pressure of the fluid flowing through the valve 100, as will be described in more detail below with respect to FIG. 2. While the valve assembly 112 and the pressure sensor assembly of the valve 100 are shown in-line with one another and with the inlet port 106 and outlet port 110, the valve 100 can have a variety of other configurations, and the valve assembly 112, the pressure sensor assembly, the inlet port 106, and the outlet port 110 can be positioned at various locations relative to one another. For example, the inlet port 106 can extend at a right angle with respect to the pressure sensor assembly such that the inlet port 106 extends in a direction substantially transverse to a longitudinal axis of the valve 100. The valve assembly 112 itself can also have a variety of configurations. By way of non-limiting example, exemplary valves are described in U.S. Pat. Nos. 3,886,948, 4,332,255, 4,387,715, 4,551,128, 4,595,390, 4,615,691, 4,772,257, and 5,928,182, all of which are hereby incorporated by reference in their entireties.

As shown, the valve 100 can include a chipless RF tag 114 disposed in the reservoir 108 for measuring a pressure of the fluid flowing through the valve 100 and for communicating with an external reading device, as will be described in more detail below. In some embodiments, the RF tag 114 can include a chip to store data and can communicate stored data to an external reading device. The pressure of fluid in the reservoir 108, can directly or indirectly (e.g., through a flexible membrane) push against the RF tag 114 and change electrical properties (e.g., capacitance) of circuitry in the RF tag 114. One or more of these changed properties can result in a change in the response (or a characteristics of the response) of the RF tag 114 to a signal from a reading device, thereby indicating and measuring pressure, e.g., intra-cranial pressure ("ICP"). For example, the characteristic can include one or more electromagnetic characteristics, such as resonance frequency, Q factor, or harmonic spectra of the RF tag 114. As will be explained in more detail below, the electromagnetic properties can be determined and/or altered by changes in the physical/electrical characteristics of circuitry in the RF tag 114.

The relative positions of the elements shown in the valve 100 of FIG. 1 can vary in different embodiments. For example, while the valve assembly 112 and the RF tag 114 are shown in-line with one another and with the inlet and outlet ports 106, 110, and the RF tag 114 is positioned upstream of the valve 100, the valve 100 can have a variety of other configurations and the valve assembly 112, the RF tag 114, the inlet port 106, and the outlet port 110 can be positioned at various locations relative to one another. For example, as shown in FIG. 2, the RF tag 114 is disposed in an offset tag housing area 200 of the reservoir 108 but is in fluid communication with the reservoir 108.

The housing 102 can be formed from a variety of materials. In an exemplary embodiment, however, the housing 102 is formed from a flexible, biocompatible material. Suitable materials include, for example, polymers such as silicones, polyethylene, and polyurethanes, all of which are known in the art. The housing 102 can also optionally be formed from a radio-opaque material. A person skilled in the art will appreciate that the materials are not limited to those listed herein and that a variety of other biocompatible materials can be used.

The valve 100 and/or the RF tag 114 can also optionally include a coating 116 that is adapted to hermetically seal all or at least a portion of the valve 100, the RF tag 114, and/or other components such as a sensor, an antenna, a connector, etc. The coating 116 can be applied to only a portion of the RF tag 114, to the entire RF tag 114, and/or to the valve 100. The RF tag 114 and the valve 100 can be coated separately with different coatings, or alternatively, together in a single coating, which can seal the RF tag 114 in place with the valve 100. In the embodiment shown in FIG. 4 in which the RF tag 114 is disposed in the valve 100, the RF tag 114 is pre-coated prior to coupling the sensor assembly to the housing 102. Once coated, the RF tag 114 can be appropriately positioned. An adhesive or other mating technique can be used to affix the RF tag 114 within the housing 102, as shown in FIG. 5, however, in some embodiments it can be useful to allow the RF tag 114 to be removed from the valve 100 if necessary.

Alternatively, the valve 100 can be coated after the RF tag 114 is disposed in the reservoir 108 to form a protective sheath over the RF tag 114 and the housing 102. The ports 106, 110 can be protected from any coating applied thereto, formed after the coating is applied, or be cleared of any coating applied thereto to allow fluid to flow therethrough. In other embodiments, only certain components of the valve 100 can be coated. A person skilled in the art will appreciate that a variety of other techniques can be used to seal the RF tag 114 and/or other components of the valve 100.

The material used to form the coating 116 can vary, and a variety of techniques can be used to apply the coating. By way of non-limiting example, suitable materials include polyurethane, silicone, solvent-based polymer solutions, and any other polymer that will adhere to the components to which it is applied to, and suitable techniques for applying the coating include spray-coating or dip-coating.

As previously mentioned, the RF tag 114 can be adapted to measure a pressure of an external environment, e.g., of fluid in the reservoir 108 and/or fluid flowing through the valve 100 through the reservoir 108. In use, the pressure of fluid in the valve 100 can impinge on the RF tag 114 through a coating, a deflectable membrane as described above, or in some embodiments directly contact the RF tag 114. The pressure from the fluid (or other external conditions) can alter the physical and electrical properties of the RF tag 114 which in turn can alter the electromagnetic behavior of the RF tag 114 in a measurable and predictable manner. In other words, the behavior of the RF tag 114 can change in response to a stimulus. The behavior manifests as a change in a measurable characteristic (for example, an electromagnetic characteristic such as resonant frequency, harmonic spectra, and/or quality (Q) factor) in the response of the RF tag 114 to an interrogating wireless signal (e.g., a time-varying electromagnetic field) directed at it from an external reader. Any characteristic, or a combination thereof, can be measured or analyzed to indicate CSF pressure.

In some embodiments, the RF tag 114 can be a planar electromagnetic resonator having capacitive and inductive elements therein, and in some embodiments it can have an electromagnetically active material located between its capacitive and inductive elements. For many embodiments, the RF tag 114 can be generally represented by a resonator circuit 300 as shown in FIG. 3. As shown, the circuit 300 includes a capacitor 302, an inductor 304, and an intrinsic resistance 306 (e.g., a dielectric between two conductors forming the capacitor 302). When the RF tag 114 is embedded in the valve 100, shifts in the resonant frequency of the circuit 300 can be monitored on a continuous or intermittent basis to measure pressure of fluid flowing through the valve 100. The fluid pressure can detectably change a distance between the conductors of the capacitor 302, where the distance can affect an electrical property of the circuit 300 that is manifested as a change in a resonant frequency or other electromagnetic characteristic. The resonant frequency of the circuit 300 or other characteristic can be detected in a variety of ways, such as by measuring power reflected from the circuit 300 or measuring decaying circulating power of the circuit 300 following a outside signal (e.g., from a telemetry device). FIG. 4 illustrates an example of a graph showing an output signal of the circuit 300 when introduced to an outside signal. The reflected power of the circuit 300 is at a minimum at the resonant frequency, where ω can be expressed as:

$$\omega = 2\pi f = \frac{1}{\sqrt{LC}}$$

with f representing the resonant frequency, L representing inductance of the inductor 304, and C representing capacitance of the capacitor 302. FIG. 5 illustrates another example of a graph showing an output signal of the circuit 300 when introduced to an outside signal. The reflected power of the circuit 300 in this example is at a maximum at the resonant frequency.

Further information on RF tags, including techniques for interrogating them and examples of them, can be obtained from U.S. Pat. Nos. 6,025,725, and 6,278,379, and U.S. Patent Application Publication No. 2004/0134991, all of which are hereby by incorporated by reference in their entireties.

The shape, technical specifications, and size of the RF tag 114 can vary widely. In many embodiments, a relatively small RF tag can be used so as to minimize the footprint of the tag in the device, for example with dimensions in a range of about 5 mm to 10 mm, but in other embodiments, tags with dimensions of about 3 mm to 50 mm can be used and any size is possible. The RF tag 114 can be adapted to be in communication with an external device (e.g., by having an antenna) and to store data.

The RF tag 114 can have any shape, such as elliptical, circular, or rectangular (including square), and can have virtually any size. The following table (Table 1) lists, by way of example only, available RF tags suitable for use with the devices and methods described herein. Passive as well as semi-passive and active tags can be used, although semi-passive and active tags sometimes are larger than passive tags because they can incorporate an internal battery, e.g., for power purposes.

tank circuit) and can be powered from the reading device signal. Such an RF tag can be advantageous due to its relatively low power requirements, and need not have the ability to communicate stored data or "identify" itself. However, in many embodiments the RF tag 114 can provide, in addition to the pressure sensor functionality described above, data storage for storing additional information related to the application. In other words, the RF tag 114 can include an RF chip, which in some cases can be an off-the-shelf component. An example of chip-based tags are the commonly used RF identification tags. Some of these RF identification tags provide minimal information (such as a TRUE or FALSE value), while others can store several bytes of data. A chip-based RF tag can include memory circuitry, a separate antenna, and/or simple digital logic, which in many embodiments can reside on the same substrate or package as the circuitry provided for sensing pressure (for example, the tank circuit mentioned above). Providing both circuitry for measuring pressure and memory, or other circuitry, can be advantageous in many applications to save space and to provide increased functionality. Such RF tags also can be powered by the reading device signal. In alternative embodiments, RF tags with batteries and/or processing circuitry can also be used if their size, typically relatively large, can be accommodated by the application.

Various kinds of data can be stored in the memory of an RF tag. For example, in one embodiment, the RF tag 114 can include a memory for storing data related to the patient and/or sensor. By way of non-limiting example, the RF tag 114 can store sensed pressure data, sensor identification information (e.g., implantation date, sensor type, and sensor identifier code), sensor calibration data, historical data stored from the sensor, tag identification information (e.g., implantation date, tag type, and tag identifier code), and/or patient data (e.g., desired CSF flow rate, previous sensor measurements, and

| | Frequency | | | | | |
|---|---|---|---|---|---|---|
| Tag Type | 125 KHz | 5-7 MHz | 13.56 MHz | 303/433 MHz | 860-960 MHz | 2.45 GHz |
| Passive | ISO11784/5, 14223 ISO18000-2 | ISO10536 iPico DF/iPX | (ISO15693) (ISO15693) MIFARE (ISO14443) Tag-IT (ISO15693) ISO18000-3 | — | ISO18000-6 Electronic Product Code ("EPC") Class 0 EPC Class 1 EPC GEN II Intellitag tolls (Title 21) rail (Association of American Railroads ("AAR") S918) | ISO18000-4 Intellitag μ-chip |
| Semi-Passive | — | — | — | — | rail (AAR S918) Title 21 | ISO18000-4 Alien BAP |
| Active | — | — | — | Savi (American National Standards Institute ("ANSI") 371.2) ISO18000-7 RFCode | — | ISO18000-4 WhereNet (ANSI 371.1) |

It should be understood that in some embodiments, the RF tag 114 can be chipless, and its electromagnetic parameters, as altered by the physical force of pressure against it, can be used to determine pressure. The RF tag 114 need not have the capability to store data or to communicate according to a protocol, and need not have processing circuitry or digital logic. A chipless RF tag can provide a circuit (for example, having measurable electromagnetic characteristics, such as a patient medical history). An external reading device, described further below, can read and/or store data in such an RF tag 114. In use, for example, an external reading device can read a sensed pressure from the RF tag 114, and can store data representing or related to the sensed pressure in the memory of the RF tag 114. In many embodiments, the external reading device can provide the power the RF tag 114 requires to operate.

Figure 6:
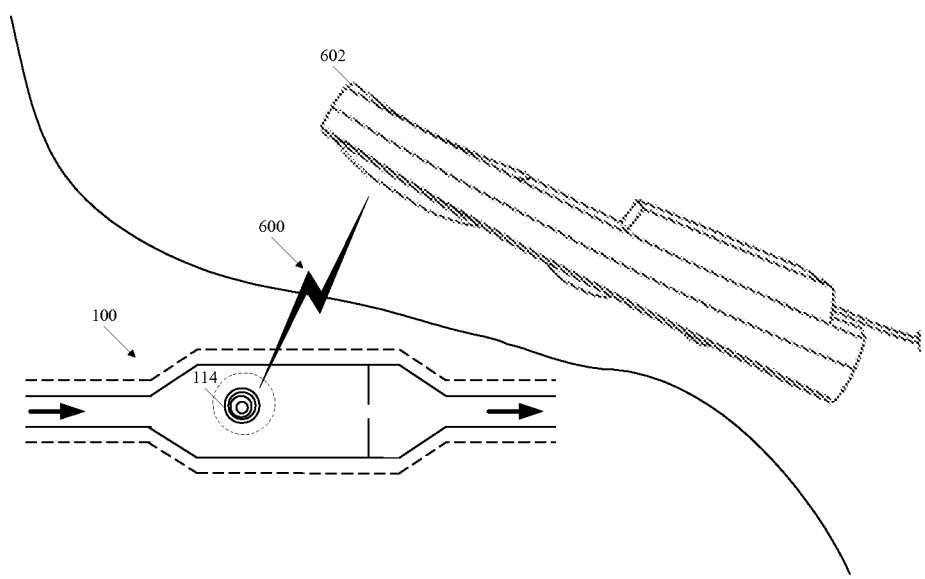
FIG. 6 is a cross-sectional view of the implantable valve of FIG. 1 implanted in a body and an exemplary embodiment of an external radio frequency telemetry system disposed adjacent thereto outside the body for reading a signal from the implantable valve.
Figure 7:
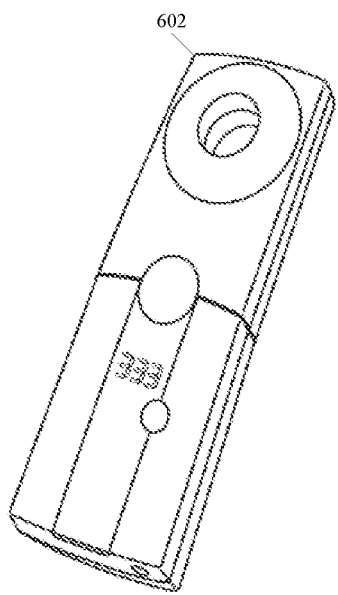
FIG. 7 is a perspective view of an exemplary embodiment of an external radio frequency telemetry system.
Figure 8:
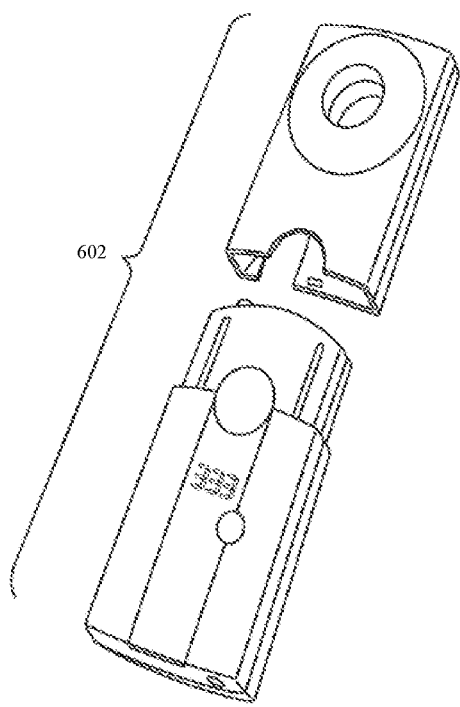
FIG. 8 is a perspective view of the external radio frequency telemetry system of FIG. 7 in a disassembled configuration.

As illustrated in FIG. 6, the RF tag 114 can be adapted to interact with a wireless signal 600 from an external reading device 602, such as an RF telemetry device (shown in more detail in FIGS. 7-8). The reading device 602 can emit a signal 600 at one frequency or over a range of frequencies and can receive a response thereto, e.g., from the RF tag 114 or a sensor. The response to the RF tag 114 to the wireless signal 600 can communicate information from the RF tag 114. In the case of a chipless tag, a characteristic of the response from the tag can indicate a measured pressure, as explained above. In the case of a chip-based RF tag having memory associated therewith, the response of the tag can also include (e.g., according to a communication protocol) the information stored in its memory.

Virtually any type of external reading device can be used as the reading device 602. In one exemplary embodiment, the reading device 602 can include an RF module (e.g., transmitter and receiver), a control unit (e.g., microcontroller), a coupling element to the transponder (e.g., antenna), and an additional interface (e.g., Recommended Standard (RS) 232, RS-485, Firewire, USB, Bluetooth, ZigBee, etc.) to enable communication with another external device (e.g., a personal computer). The reading device 602 can provide the power required by the RF tag 114 to operate, e.g., through the coupling element. The reading device 602, as shown in FIG. 8, can be positioned adjacent to the RF tag 114 to telemetrically communicate with the RF tag 114, and thereby obtain and/or transmit data. The embodiment of the reading device 602 in FIG. 6 is shown in a front perspective in FIG. 7 and in a front perspective, disassembled configuration in FIG. 8.

Figure 9:
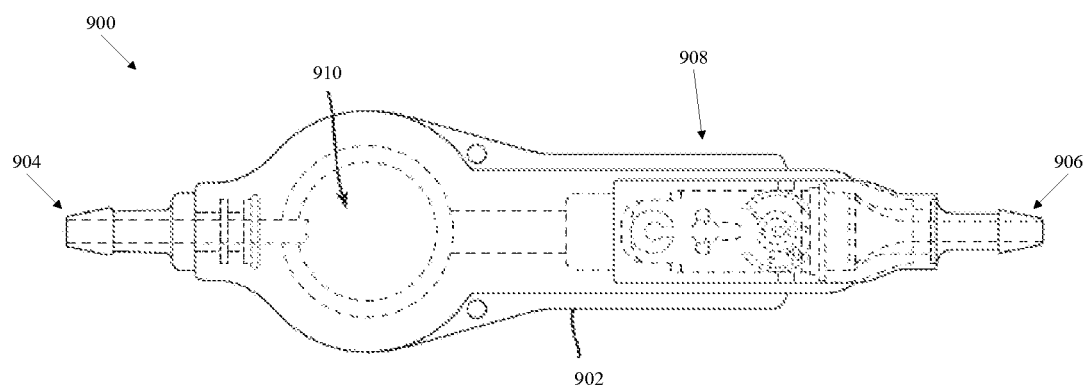
FIG. 9 is a top view of another embodiment of an implantable valve.
Figure 10:
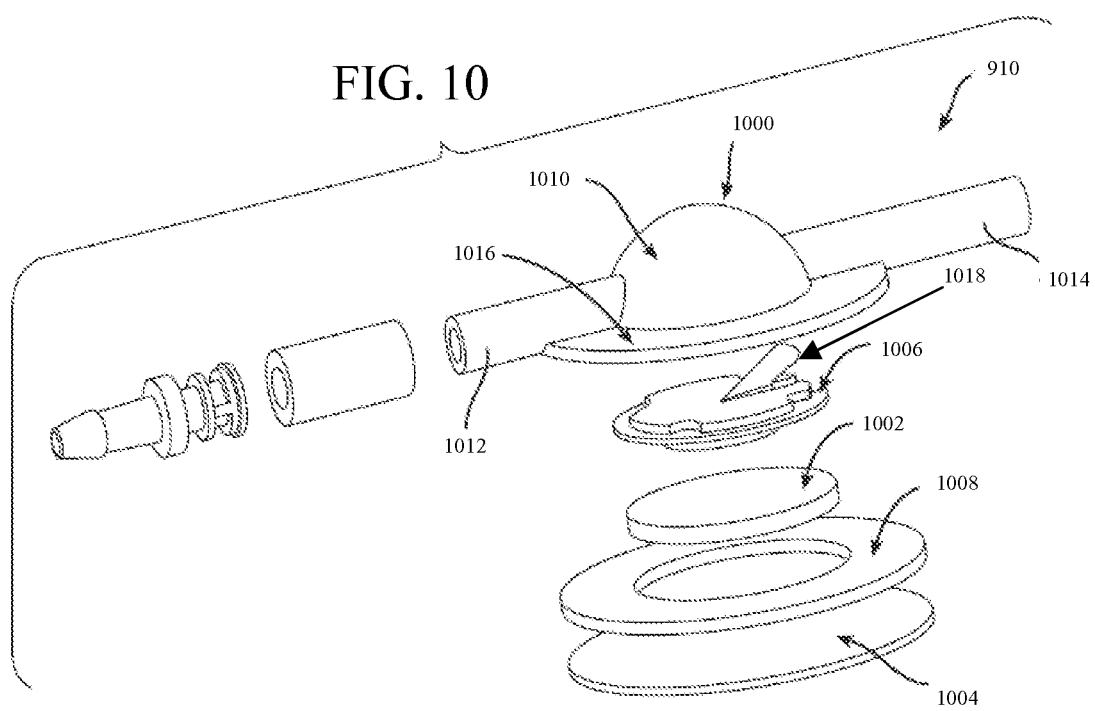
FIG. 10 is an exploded view of a portion of the implantable valve shown in FIG. 9.

FIGS. 9 and 10 illustrate another exemplary embodiment of an implantable valve 900 having an RF tag therein for sensing pressure. As shown, the implantable valve 900 has a valve housing 902 with an inlet 904 and an outlet 906. The valve housing 902 can contain a valve assembly or mechanism 908 for controlling the flow of fluid from the inlet 904 to the outlet 906, and a pressure sensing assembly 910 for measuring a pressure of the fluid flowing through the valve 900.

The pressure sensor assembly 910 shown in FIG. 9 is provided in more detail in FIG. 10. As shown, the pressure sensor assembly 910 can include a housing with a septum 1000 defining a fluid reservoir 1010 therein. An RF tag 1002 can be disposed in the reservoir 1010 for sensing pressure therein, supported by a washer 1008 and a backing 1004. The sensor assembly 910 can also include a needle guard 1006 disposed between the reservoir and the RF tag 1002, for example to protect the RF tag but still allow for the RF tag 1002 to be in fluid communication with the reservoir and thus obtain an accurate pressure measurement.

The septum 1000 can have a variety of shapes and sizes, but in the illustrated exemplary embodiment the septum 1000 has a generally hemi-spherical or domed portion that defines a reservoir 1010 therein. The reservoir can be in fluid communication with an inlet tube 1012 that couples to the inlet 904 of the valve 900, and an outlet tube 1014 that couples to the outlet 906 of the valve 900. When the septum 1000 is mated to the backing 1004, the reservoir 1010 defined by the septum 1000 is sealed, thereby allowing fluid to flow from the inlet 904 of the valve 900, through the tag housing 1000, through the valve 900, and out the outlet 906. A flange 1016 can be formed at around the base of the septum allow the device to be secured to tissue. For example, the flange 1016 can include one or more suture holes formed therein for receiving suture to attach the flange 1016 to tissue.

As shown, an RF tag 1002 can be disposed in the reservoir 1010 for sensing the pressure of fluid therein. The RF tag 1002, which can have any or all of the features of the RF tag 114 described previously, is shown as having a substantially circular shape, and can communicate with an external RF reading device, as previously described. The RF tag 1002 can also include a fluid-impermeable coating disposed therearound, as previously described, to protect the RF tag 1002 from fluid flowing through the reservoir 1010. A washer 1008 and a backing 1004 can provide support or a securing means for the RF tag 1002. As shown, the washer and the backing 1004 are disposed underneath the RF tag 1002, however a wide variety of configurations are possible. The washer 1008 can also be configured such that the RF tag 1002 is sub-flush with the washer 1008. Such a configuration can protect the RF tag 1002 from potential damage if the domed portion of the septum 1000 is depressed to pump fluid through the reservoir, to test the valve 900 or to clear the valve 900 from debris, etc.

As further shown in FIG. 10, the sensor assembly 910 can also include a needle guard 1006 for protecting the RF tag 1002. In particular, the needle guard 1006 can protect the RF tag 1002 from coming into contact with the domed portion of the septum 1000 when the domed portion is depressed, as the needle guard 1006 can be positioned between the RF tag 1002 and the septum 1000. The needle guard 1006 can also be provided to protect the RF tag 1002 from a needle inserted through the septum 1000 and into the reservoir 1010. A needle may be used to deliver or withdraw fluid from the reservoir through the septum 1000. While the shape of the needle guard 1006 can vary depending on the shape of the sensor assembly 910, in an exemplary embodiment, as shown, the needle guard 1006 has a substantially planar, circular shape and it is adapted to be disposed between the domed portion of the septum 1000 and the RF tag 1002. The needle guard 1006 can, however, include an opening formed therein and positioned adjacent to the microchip RF tag 1002 to allow fluid in the reservoir 1010 to come into contact with the RF tag 1002 or membrane or covering over the RF tag 1002. In an exemplary embodiment, a flange or protective member 1018 is disposed over the opening, without blocking the opening from fluid flow, to prevent a user from accidentally inserting a needle through the opening. A person skilled in the art will appreciate that a variety of other techniques can be used to protect the RF tag 1002.

In use, the RF tag 1002 can sense the pressure of fluid in through the reservoir 1010. In particular, the inlet 904 of the valve 900 can be coupled to a ventricular catheter for receiving fluid flow from the ventricles, and the outlet 906 can be coupled to a drainage catheter. As the fluid enters the reservoir 1010, the pressure of the fluid will apply a force to the RF tag 1002 and change one or more of its electromagnetic characteristics, thereby allowing the fluid pressure to be measured, as was described previously. The sensed pressure can be communicated to an external reading device, such as the external reading device 602 shown in FIGS. 6-8, as previously described. As mentioned previously, in many embodiments the RF tag 1002 can include a memory, and the external reading device 602 can be used to store data representing or related to the sensed pressure (or other data) back in the memory of the RF tag 1002.

Figure 11:
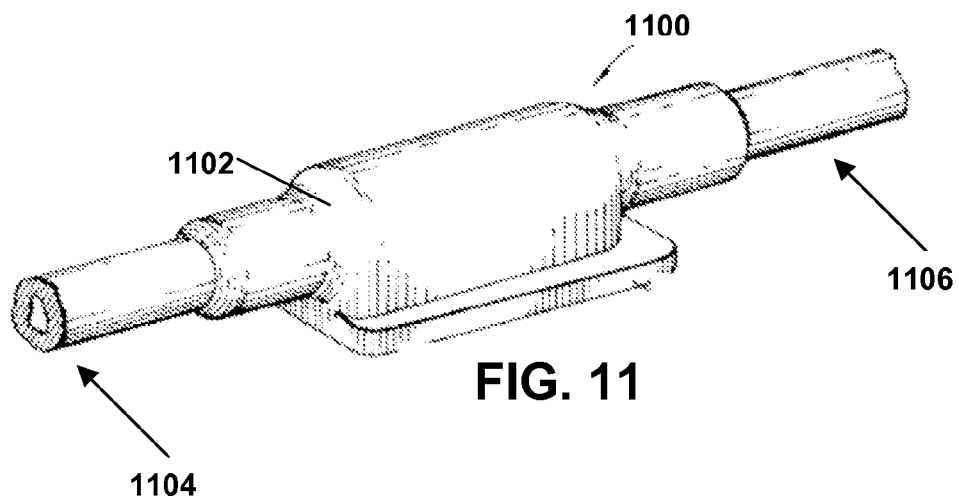
FIG. 11 is a perspective view of another exemplary embodiment of an implantable valve.
Figure 12:
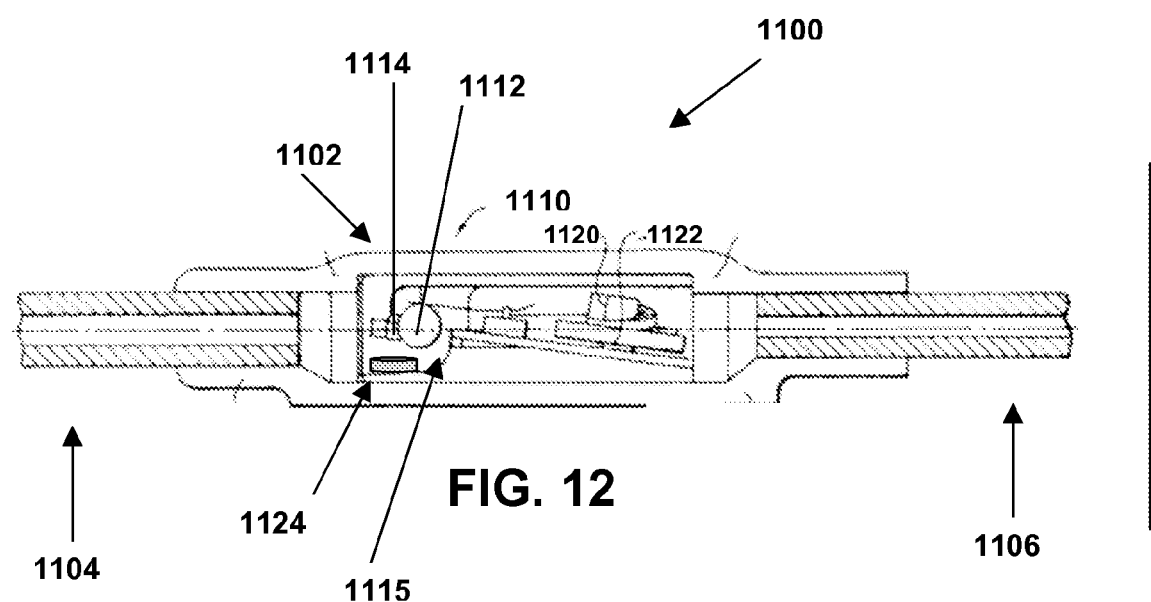
FIG. 12 is a side cutaway view of the valve shown in FIG. 11 showing a radio frequency tag disposed therein for sensing pressure.
Figure 13:
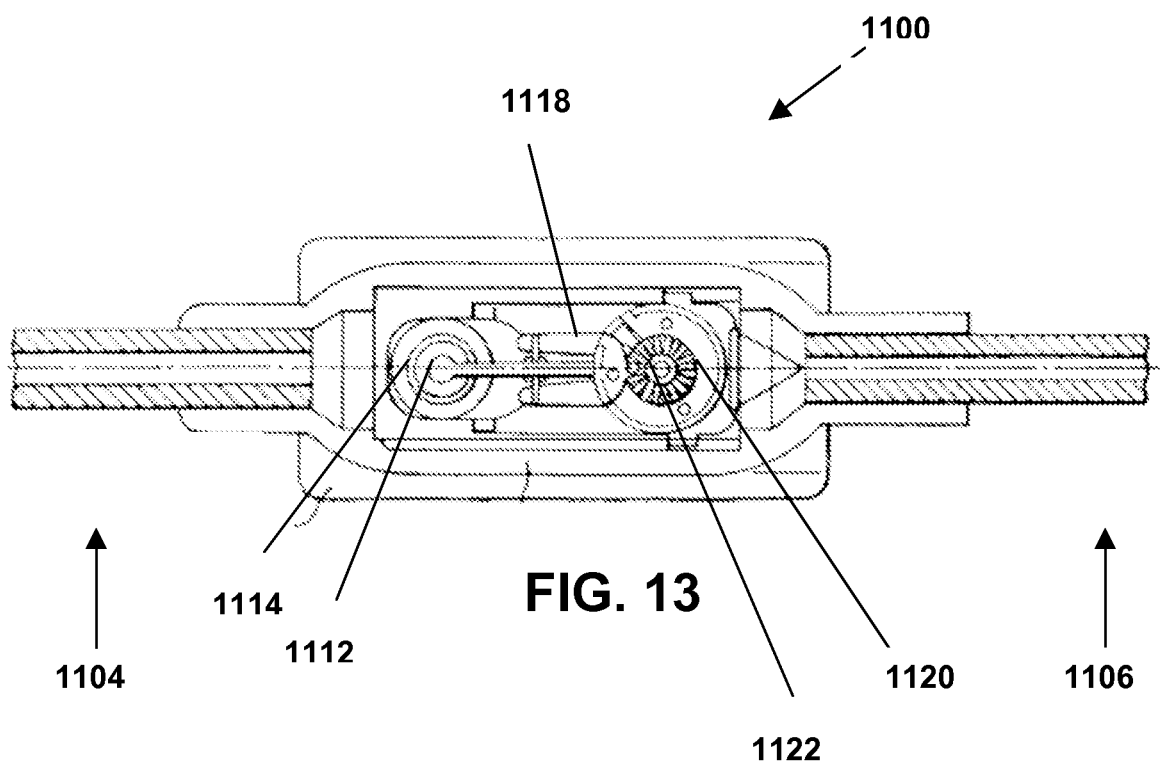
FIG. 13 is a top cutaway view of the valve shown in FIG. 12.

FIGS. 11-13 illustrate another exemplary embodiment of an implantable valve 1100 having a housing 1102 for receiving fluid flow between a valve inlet 1104 and an valve outlet 1106, and valve assembly 1110 for controlling fluid flow therethrough. As shown in FIGS. 11-13, the housing 1102 has a substantially linear configuration. A RF tag 1124 can be disposed in the housing 1102 in an area between the inlet 1104 and the valve assembly 1112. In some embodiments, the area can be enlarged to form a larger area or larger reservoir (for example, as shown in FIGS. 9-10) and/or can be located elsewhere in the valve 1100. In use, the pressure of the fluid on the RF tag 1124 can alter one or more of the electromagnetic characteristics thereof, which can be detected in its response to a signal from an external reader, as previously described.

As shown, the implantable valve 1100 shown in FIGS. 11-13 can also include a valve assembly 1110 for controlling the flow of fluid according to one of a plurality of selectable pressure settings. As shown, the valve assembly 1110 includes a ball 1112 engaging a valve seat 1114, which sits in a valve opening 1115 in the fluid path between the valve inlet 1104 and the valve outlet 1106, and which controls fluid flow therethrough. The ball 1112 can be under the force of a spring 1118 or other biasing element. The spring 1118 can be in the form of an arm extending from an adjustment mechanism, which as shown in FIGS. 12-13 is a stepper motor 1120, to the upper surface of the ball 112 such that it exerts a downward force thereon. The stepper motor 1120 includes a stepped surface, each step representing a pressure setting. As can be seen in FIGS. 12-13, the rotational position of the stepper motor 1120 can determine the force of the spring 1118 on the ball 1112 and thereby control the pressure at which fluid will flow through the valve opening 1115. In use, the rotational position of the stepper motor 1120 can be controlled by an external programmer, for example via a changing electromagnetic field applied to magnetic field elements disposed about a central axis 1122 of the stepper motor 1120 to rotate the stepper motor in a controlled fashion. The magnetic field elements can be magnets shaped and positioned with respect to the axis or rotor of the stepper motor 1120. More information on the operation of stepper motors and such valves can be obtained from U.S. Pat. Nos. 5,928,182; 4,772,257; and 4,615,691, all of which are hereby incorporated by reference in their entireties.

In another aspect, a method for sensing pressure in a medical device, such as any of the valves previously described, is provided. Referring for illustrative purposes only to FIG. 9, the inlet 904 of the valve 900 can be coupled to a proximal end of a ventricular catheter that has its distal end positioned in a patient's ventricle. The valve 900 can be implanted in a patient, e.g., subcutaneously behind the ear, elsewhere on the head, in a shoulder region (see FIG. 6, for example), torso, or virtually anywhere. The typically flexible catheter can extend through the patient to the ventricle.

A drainage catheter can be coupled to the outlet 906 of the valve 900, where the drainage catheter can extend through the patient to an area where excess fluid can safely drain. The rate of fluid flowing through the valve 900 from the inlet 904 to the outlet 906 can be controlled by the valve assembly 908. The pressure of fluid (e.g., CSF) within the valve 900 or flowing through the valve 900 can be obtained by measuring a response of the RF tag 1002 (e.g., using a reading device 602) disposed in the reservoir under the domed portion 1010. The method can further include storing data (for example, data related to or representing a sensed pressure) back into the RF tag 1002 using an external device such as the reading device 602. In many embodiments, the reading device 602 can provide the power required by the RF tag 1002 to operate. The method can also include implanting the RF tag concurrently or subsequently (e.g., as a replacement or retrofit) with the valve or other medical device.

Further information on wireless shunts can be obtained from U.S. patent application Ser. No. 11/931,041, entitled "Wireless Pressure Setting Indicator" by Salim Kassem, U.S. patent application Ser. No. 11/931,127, entitled "Wireless Flow Sensor" by Salim Kassem, and U.S. patent application Ser. No. 11/931,151, entitled "Wireless Pressure Sensing Shunts" by Salim Kassem, all of which are being filed on the same date as the present application and which are hereby incorporated by reference in their entirety. Also incorporated by reference in its entirety is co-pending, commonly assigned U.S. patent application Ser. No. 10/907,665, entitled "Pressure Sensing Valve" and published as U.S. Publication No. 2006-0211946 A1.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, glass, and any other material that is biologically compatible and non-toxic to the human body.

One skilled in the art will appreciate further features and advantages based on the above-described embodiments. Accordingly, the description is not to be limited by what has been particularly shown and described, except as indicated by the appended claims. All publications and references cited herein are expressly incorporated herein by reference in their entirety.

What is claimed is:

1. An implantable valve, comprising:
   a housing having a reservoir adapted to receive fluid flow therethrough between an inlet port and an outlet port, the housing having a top, a bottom, and opposed sides, the inlet port and the outlet port defining a longitudinal axis of the housing along which the fluid flows, the reservoir being defined in part by a dome-shaped portion extending radially outward in a first direction from the longitudinal axis, the reservoir being positioned along the longitudinal axis of the housing, and the reservoir having an offset tag housing area that is offset and downstream from the dome-shaped portion and that extends radially outward in a second direction from the longitudinal axis, the first direction being transverse to the second direction;
   a valve assembly disposed within the first portion of the housing and adapted to control a rate of fluid flowing through the housing; and
   a radio frequency tag comprising a chipless circuit disposed within the offset tag housing area with no radio frequency tag disposed in or under the dome-shaped portion, the chipless circuit being adapted to change one or more electromagnetic characteristics in response to pressure applied thereto by fluid in the reservoir and to produce a response to a wireless signal characterized by the one or more electromagnetic characteristics that correlates to a pressure of fluid in the reservoir.

2. The implantable valve of claim 1, further comprising a needle guard disposed within the housing and adapted to protect the radio frequency tag from a needle penetrating into the housing.

3. The implantable valve of claim 1, wherein the one or more electromagnetic characteristics is selected from resonant frequency, harmonic spectra, and Q factor.

4. The implantable valve of claim 1, wherein the pressure of fluid in the reservoir detectably changes any of the shape and the capacitance of the radio frequency tag so as to change the one or more electromagnetic characteristics thereof.

5. The implantable valve of claim 1, wherein
the circuit includes an inductor and a capacitor connected to form an electrical circuit having a resonant frequency, the capacitor comprising a pair of conductors separated by a dielectric; and
a pressure of fluid in the reservoir detectably changes a distance between the pair of conductors,
wherein the distance between the pair of conductors correlates to any of the resonant frequency, harmonic spectra, and Q factor of the electric circuit.

6. The implantable valve of claim 1, wherein the dome-shaped portion defines a needle-penetrable septum.

* * * * *